(12) United States Patent
Kawanaka et al.

(10) Patent No.: US 8,093,184 B2
(45) Date of Patent: Jan. 10, 2012

(54) PESTICIDAL COMPOSITION

(75) Inventors: Hideo Kawanaka, Toyonaka (JP);
Yoshinao Sada, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1504 days.

(21) Appl. No.: 11/476,655

(22) Filed: Jun. 29, 2006

(65) Prior Publication Data

US 2007/0066486 A1    Mar. 22, 2007

(30) Foreign Application Priority Data

Jul. 4, 2005  (JP) ................. 2005-194690
Mar. 17, 2006  (JP) ................. 2006-074187

(51) Int. Cl.
*A01N 57/00*  (2006.01)
(52) U.S. Cl. .................................... 504/128
(58) Field of Classification Search .................. 504/127, 504/128
See application file for complete search history.

(56) References Cited

U.S. PATENT DOCUMENTS

| | | | |
|---|---|---|---|
| 5,698,492 A | 12/1997 | Sakaki et al. | |
| 6,165,939 A | 12/2000 | Agbaje et al. | |
| 6,569,809 B1 | 5/2003 | Sato et al. | |
| 6,583,087 B2 | 6/2003 | Ueda | |
| 2005/0101488 A1 | 5/2005 | Tanedani | |

FOREIGN PATENT DOCUMENTS

| | | |
|---|---|---|
| EP | 0244754 A1 | 11/1987 |
| EP | 0354346 A1 | 2/1990 |
| EP | 1 095 564 A2 | 5/2001 |
| GB | 2169806 A | 7/1986 |
| JP | 2003-252704 A | 9/2003 |
| JP | 2005-2108 A | 1/2005 |
| WO | WO-99/27781 A1 | 6/1999 |
| WO | WO-00/64256 A1 | 11/2000 |

OTHER PUBLICATIONS

Office Action dated May 18, 2010 for Chinese Patent Application No. 200610103113.X.
Japanese Office Action dated Oct. 18, 2011, for Application No. 2006-176476.

*Primary Examiner* — Alton Pryor
(74) *Attorney, Agent, or Firm* — Birch, Stewart, Kolasch & Birch, LLP

(57) ABSTRACT

A pesticidal composition comprising (a) a water-insoluble solid pesticidal ingredient, (b) a salt of N-phosphonomethylglycine, (c) a salt of polyoxyalkylene alkyl ether phosphate ester, (d) a salt of polyoxyalkylene polystyrylphenyl ether phosphate ester, (e) a thickener and (f) water, wherein said pesticidal ingredient is suspended in the aqueous continuous phase as solid state, is excellent in suspension stability.

6 Claims, No Drawings

PESTICIDAL COMPOSITION

TECHNICAL FIELD

The present invention relates to a pesticidal composition.

BACKGROUND ARTS

Pesticidal compositions containing two or more active ingredients are used for various objects.

For example, though salts of N-phosphonomethylglycine are widely used as active ingredients of non-selective herbicides, they require time to express their herbicidal effects; thus, proposed were some herbicidal compositions mixed with the other herbicidal ingredient having rapid efficacy. Typical herbicidal ingredient having rapid efficacy is a protoporphyrinogen oxidase inhibitor. However, it is generally solid and water-insoluble though the salts of N-phosphonomethylglycine are freely soluble in water; thus it has been desired to develop the mixed herbicidal composition that has good formulation stability.

U.S. Pat. No. 5,698,492, U.S. Pat. No. 6,583,087 and JP 2003-252704A discloses pesticidal compositions containing a water-insoluble herbicidal ingredient and another water-insoluble herbicidal ingredient. However, it is further desired to develop the mixed herbicidal composition that has good formulation stability and contain no or little organic solvent.

DISCLOSURE OF THE INVENTION

The present invention provides excellent suspension stability of an aqueous pesticidal formulation by using two kinds of specific anionic surfactants, wherein a water-insoluble solid pesticidal ingredient is suspended in the aqueous continuous phase in which a salt of N-phosphonomethylglycine is dissolved.

The present invention provides a pesticidal composition comprising (a) a water-insoluble solid pesticidal ingredient, (b) a salt of N-phosphonomethylglycine, (c) a salt of polyoxyalkylene alkyl ether phosphate ester, (d) a salt of polyoxyalkylene polystyrylphenyl ether phosphate ester, (e) a thickener and (f) water, and further optionally (g) an antifreezing agent, wherein said pesticidal ingredient is suspended in the aqueous continuous phase as solid state. The pesticidal composition has excellent suspension stability wherein the pesticidal ingredient is suspended in the aqueous continuous phase in which a salt of N-phosphonomethylglycine is dissolved. In the present invention, the term "continuous phase" means dispersion medium, namely liquid in a disperse system in which solids are suspended.

Preferable embodiment is a pesticidal composition comprising (a) 0.5 to 50 w/v % of a water-insoluble solid pesticidal ingredient, (b) 5 to 60 w/v % of a salt of N-phosphonomethylglycine, (c) 0.5 to 15 w/v % of a salt of polyoxyalkylene alkyl ether phosphate ester, (d) 0.5 to 10 w/v % of a salt of polyoxyalkylene polystyrylphenyl ether phosphate ester, (e) 0.01 to 10 w/v % of a thickener and (f) 20 to 90 w/v % of water, wherein said pesticidal ingredient is suspended in the aqueous continuous phase as solid state. More preferable embodiment is a pesticidal composition comprising (a) 1 to 30 w/v % of a water-insoluble solid pesticidal ingredient, (b) 10 to 50 w/v % of a salt of N-phosphonomethylglycine, (c) 0.5 to 15 w/v % of a salt of polyoxyalkylene alkyl ether phosphate ester, (d) 0.5 to 10 w/v % of a salt of polyoxyalkylene polystyrylphenyl ether phosphate ester, (e) 0.01 to 5 w/v % of a thickener and (f) 20 to 90 w/v % of water, wherein said pesticidal ingredient is suspended in the aqueous continuous phase as solid state.

The water-insoluble solid pesticidal ingredient is solid at 25° C. and has a solubility in water of 10 g/L or less at 25° C. Its melting point is preferably 60° C. or more. The solid pesticidal ingredient has preferably 1.2 to 3.0 of specific gravity. Examples of the solid pesticidal ingredient include insecticidal ingredients, fungicidal ingredients, herbicidal ingredients and plant growth regulating ingredients.

Examples of the insecticidal ingredients include abamectin, acrinathrin, amitraz, azadiractin, azamethiphos, azinphos-methyl, azocyclotin, bensultap, bifenthrin, bromopropylate, buprofezin, chlorfenapyr, chlorfenson, chlorfluazuron, clofentezine, coumaphos, cyfluthrin, β-cyfluthrin, cypermethrin, α-cypermethrin, θ-cypermethrin, deltamethrin, diafenthiuron, dicofol, diflubenzuron, endosulfan, esfenvalerate, etoxazole, fenazaquin, fenbutatin oxide, fenoxycarb, fenpyroximate, fipronil, fluazuron, flucycloxuron, flufenoxuron, halofenozide, hexaflumuron, hexythiazox, hydramethylnon, lufenuron, methiocarb, methoxychlor, milbemectin, novaluron, pentachlorophenol, pyridaben, rotenone, sulfluramid, tebufenozide, tebufenpyrad, tebupirimfos, teflubenzuron, tetrachlorvinphos, tetradifon, thiodicarb, tralomethrin, triflumuron and trimethacarb.

Examples of the fungicidal ingredients include azoxystrobin, benalaxyl, benomyl, bitertanol, bromuconazole, captafol, captan, carbendazim, chinomethionat, chlorothalonil, chlozolinate, cyprodinil, dichlorfluanid, dichlorophen, diclomezine, dicloran, diclocymet, diethofencarb, dimethomorph, diniconazole, dithianon, epoxiconazole, famoxadone, fenarimol, fenbuconazole, fenfuram, fenpiclonil, fentin, fluazinam, fludioxonil, fluoroimide, fluquinconazole, flusulfamide, flutolanil, folpet, hexachlorobenzene, hexaconazole, imibenconazole, ipoconazole, iprodione, kresoxim-methyl, manzeb, maneb, mepanipyrim, mepronil, methoconazole, metiram, nickel bis(dimethyldithiocarbamate), nuarimol, oxine-copper, oxolinic acid, pencycuron, phthalide, procymidone, propineb, quintozene, sulfur, tebuconazole, tecloftalam, tecnazene, thifluzamide, thiophanate-methyl, thiram, tolclofos-methyl, tolylfluanid, triadimefon, triadimenol, triazoxide, triforine, triticonazole, vinclozolin, zineb and ziram.

Examples of the herbicidal ingredients include protoporphyrinogen oxidase inhibiting herbicidal active ingredients such as azafenidin, bifenox, sulfentrazone, pyraflufen-ethyl, flumicrolac-pentyl and flumioxazin, aclonifen, atrazine, bensulfuron-methyl, benzofenap, bromobutide, bromofenoxim, chlomethoxyfen, chlorbromuron, chlorimuron-ethyl, chlornitrofen, chlorotoluron, chlorthal-dimethyl, clomeprop, dymron, desmedipham, dichlobenil, diflufenican, dimefuron, dinitramine, diuron, ethametsulfuron-methyl, fenoxapropethyl, flamprop-methyl, flazasulfuron, flumetsulam, fluthiacet-methyl, flupoxam, fluridone, flurtamone, isoproturon, isoxaben, isoxapyrifop, lactofen, lenacil, linuron, mefenacet, methabenzthiazuron, metobenzuron, naproanilide, neburon, norflurazon, oryzalin, oxadiazon, oxyfluorfen, phenmedipham, prodiamine, prometryn, propazine, propyzamide, pyrazolynate, pyrazosulfuron-ethyl, pyributicarb, quinclorac, quizalofop-ethyl, rimsulfuron, siduron, simazine, terbuthylazine, terbutryn, thiazopyr, trakoxydime and trietazine.

Examples of the plant growth regulating ingredients include 6-benzylaminopurine, cyclanilide, flumetralin, forchlorfenuron, inabenfide, 2-(1-naphthyl)acetamide, paclobutrazol, N-phenylphthalamic acid, thidiazuron and uniconazole.

In the present pesticidal composition, a part of the solid pesticidal ingredient can exist in the aqueous continuous phase as a dissolved state; however, 80% by weight or more of the pesticidal ingredient exist in the aqueous continuous phase as a solid state.

In the present pesticidal composition, the average diameter of the solid pesticidal ingredient is usually 20 μm or less, preferably 0.1 to 10 μm of volume median diameter. The volume median diameter is a value calculated by analyzing an image of numerous particles obtained with laser diffraction scattering method under Mie scattering. A typical device for measuring is Mastersizer 2000 (produced by Malvern). The volume median diameter means a value, wherein each of the volumes of smaller particles and larger particles than the value is the same, namely 50% of the total volume.

The content of the water-insoluble solid pesticidal ingredient is usually 0.5 to 50 w/v % in the present pesticidal composition.

The present pesticidal composition comprises (b) a salt of N-phosphonomethylglycine (hereinafter, referred to as N-phosphonomethylglycinate).

N-phosphonomethylglycinate is a pesticidally acceptable salt. Examples of the N-phosphonomethylglycinate include alkali metal salts (e.g. lithium salt, sodium salt, potassium salt), trialkylsulfonium salts (e.g. trimethylsulfonium salt) and ammonium salt (e.g. C1-14 monoalkylammonium salts such as isopropylammonium salt, C2-14 dialkylammonium salts such as diethylammonium salt, unsubstituted ammonium salt) of N-phosphonomethylglycine. N-phosphonomethylglycinate is commercially available (e.g. ammonium N-phosphonomethylglycinate trimethylsulfonium N-phosphonomethylglycinate), and can also be produced by known methods. The content of N-phosphonomethylglycinate is usually 5 to 60 w/v % in the present pesticidal composition, and it usually exists in the aqueous continuous phase as a dissolved state.

The weight ratio of the solid pesticidal ingredient to N-phosphonomethylglycinate in the present pesticidal composition is usually within the range between 1 to 16 and 1 to 0.1, preferably between 1 to 3 and 1 to 1.

The content of the total amount of the solid pesticidal ingredient and N-phosphonomethylglycinate is usually 5.5 to 60.5 w/v % in the present pesticidal composition.

The present pesticidal composition comprises (c) a salt of polyoxyalkylene alkyl ether phosphate ester (hereinafter, referred to as first anionic surfactant) and (d) a salt of polyoxyalkylene polystyrylphenyl ether phosphate ester (hereinafter, referred to as second anionic surfactant).

The first anionic surfactant is generally a salt produced by the phosphate ester given by the following formula:

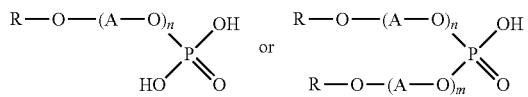

wherein R represents an alkyl group (e.g. C4-18 alkyl), A represents an alkylene group (e.g. ethylene group, propylene group) and n and m independently represent an integer of 2 to 20,
and a base such as alkali metal hydroxide and amine.

The second anionic surfactant is generally a salt produced by the phosphate ester given by the following formula:

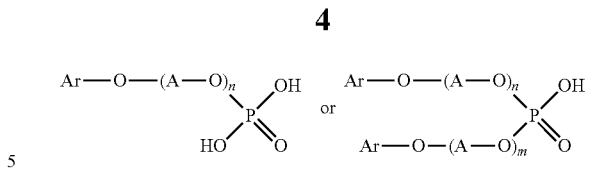

wherein Ar represents a polystyrylphenyl group (e.g. tristyrylphenyl group, distyrylphenyl group), A represents an alkylene group (e.g. ethylene group, propylene group) and n and m independently represent an integer of 2 to 20,
and a base such as alkali metal hydroxide and amine.

The above-mentioned salts of the phosphate ester are acceptable salts for surfactants and their examples include alkali metal such as sodium and potassium, alkaline earth metal such as calcium and ammonium such as $NH_4$ and $i\text{-}PrNH_3$.

Two kinds of the anionic surfactants used for the present pesticidal composition are commercially available, and the available products are mentioned below.

Examples of the first anionic surfactant include ammonium salt of polyoxyethylene alkyl ether phosphate (Geronol CF/AR produced by Rhodia Nikka) and sodium salt of polyoxyethylene oleyl ether phosphate (Phosphanol RD-720N produced by Toho Chemical).

Examples of the second anionic surfactant include potassium salt of polyoxyethylene tristyrylphenyl ether phosphate (Soprofol FLK produced by Rhodia Nikka).

With regard to the anionic surfactants used for the present pesticidal composition, the total amount of the first anionic surfactant and the second anionic surfactant in the present pesticidal composition is 3-20 w/v %, preferably 5-15 w/v %. Further, the weight ratio of the first anionic surfactant to the second anionic surfactant is usually within the range between 97 to 3 and 3 to 97, preferably between 75 to 25 and 25 to 75. The content of the first anionic surfactant is usually 0.5-15 w/v % and the content of the second anionic surfactant is usually 0.5-10 w/v % in the present pesticidal composition.

The present pesticidal composition comprises (e) thickener. Examples of the thickener include water soluble polymer such as water soluble saccharide and water soluble synthetic polymer and inorganic fine powder such as silica, magnesium silicate, aluminum silicate, magnesium aluminum silicate, bentonite, smectite, hectorite and aluminum oxide. A mixture of two or more kinds of the above-mentioned thickener is preferably used.

Examples of the water-soluble saccharide include xanthan gum, gum arabic, rhamsan gum, locust bean gum, carrageenan, welan gum, ligninsulfonic acid, starch, and carboxymethylcellulose and its salt. These water-soluble saccharides are commercially available, namely Kelzan S (produced by CP Kelco) and Kelzan ASX (produced by CP Kelco) for xanthan gum, and Celogen HE-90F (produced by Dai-ichi Kogyo Seiyaku) and Cellogen HE-600F (produced by Dai-ichi Kogyo Seiyaku) for sodium carboxymethylcellulose are available.

Examples of the water-soluble synthetic polymer include polyvinylpyrrolidone, carboxyvinyl polymer and sodium polyacrylate.

Preferable silica for the inorganic fine powder usually has 50 nm or less of primary particle diameter. Such silica is commercially available and their examples are Aerosil 200 (produced by Degussa), which is dried silica having 20 nm or less of primary particle diameter and 200 cm²/g of specific surface area, and Aerosil COK-84 (produced by Degussa), which is a mixture of Aerosil 200 and aluminum oxide.

Water-soluble saccharide or inorganic fine powder is preferably used for the present thickener in the view of formulation stability of the present pesticidal composition. Use of both water-soluble saccharide and inorganic fine powder for the present thickener is more preferable. Xanthan gum is preferable for the water-soluble saccharide and its use combined with silica or a mixture of silica and aluminum oxide is more preferable.

Further, the water-soluble saccharide that has little change of the viscosity against the change of the pH in the aqueous phase is suitable for the thickener in the present pesticidal composition. In detail, preferably used for the thickener is the water-soluble saccharide that has the change of the viscosity of its solution within the range of 1 to 3 times when it is dissolved in water having weak basic (pH 9) to weak acidic (pH 5) nature. Such water-soluble saccharide is commercially available Kelzan ASX (produced by CP Kelco) and the like.

The total content of the present thickener in the present pesticidal composition is usually 0.01 to 10 w/v %, preferably 0.1 to 5 w/v %.

The viscosity of the present pesticidal composition is preferably within the range of 500 to 300 mPa·s (measured with RB80-type viscosity meter Spindle No. 2 produced by Toki Sangyo, 6 rpm) at 20° C.

The present pesticidal composition comprises (f) water, and the content is usually 20 to 90 w/v %, preferably 30 to 70 w/v %. Ion-exchange water is preferably used for the water.

The present pesticidal composition optionally comprises (g) an auxiliary for formulation such as antifreezing agent, antifoaming agent, preservative, stabilizer, coloring agent, perfume, synergist and safener other than the first anionic surfactant, second anionic surfactant and thickener. The content of the auxiliary for formulation is usually 0 to 30 w/v %, preferably 0 to 20 w/v % in the present pesticidal composition.

Water miscible monoalcohols such as propanol and water miscible polyols such as ethylene glycol and propylene glycol are preferably used for the antifreezing agent optionally comprised in the present pesticidal composition. When an antifreezing agent is used, the content of the antifreezing agent is usually 0.5 to 30 w/v %, preferably 1 to 20 w/v %.

Examples of the antifoaming agent optionally comprised in the present pesticidal composition include silicone type antifoaming agents such as Antifoam C (commercial name of Dow Corning), Rhodosil 454 (commercial name of Rhodia), Rhodosil Antifoam 432 (commercial name of Rhodia), TSA 730 (commercial name of Toshiba Silicone) and YMA 6509 (commercial name of Toshiba Silicone) and fluorine type antifoaming agents such as Fluowet PL80 (commercial name of Clariant). When an antifoaming agent is used, the content of the antifoaming agent is usually 0.001 to 3 w/v %.

Examples of the preservative optionally comprised in the present pesticidal composition include p-hydroxybenzoate esters, salicylic acid derivatives and isothiazolin-3-one derivatives. When a preservative is used, the content of the preservative is usually 0.01 to 5 w/v %, preferably 0.05 to 3 w/v %.

Examples of the stabilizer optionally comprised in the present pesticidal composition include antioxidants such as phenol type antioxidants, amine type antioxidants, phosphorus type antioxidants and sulfur type antioxidants and UV absorbents such as benzotriazol type UV absorbents, benzophenone type UV absorbents, benzoate type UV absorbents, cyanoacrylate type UV absorbents, salicylic acid type UV absorbents and hidered amine type UV absorbents.

Examples of the coloring agent optionally comprised in the present pesticidal composition include Rhodamine such as Rhodamine B and synthetic organic food additives such as Yellow No. 4, Blue No. 1 and Red No. 2.

The present pesticidal composition may further comprise the surfactant other than the first anionic surfactants and second anionic surfactants, and examples of those surfactants include nonionic surfactants such as polyoxyalkylene alkyl ethers (e.g. polyoxyethylene alkyl ethers), polyoxyalkylene alkenyl ethers (e.g. polyoxyethylene alkenyl ethers), polyoxyalkylene alkylphenyl ethers, polyoxyalkylene castor oil, polyoxyalkylene hardened castor oil, polyoxyalkylene fatty acid esters, glycerin fatty acid esters and sorbitan fatty acid esters. When these surfactants are used, the content in the present pesticidal composition is 10 w/v % or less.

The present pesticidal composition is generally an aqueous pesticidal flowable composition wherein the solid water-insoluble pesticidal ingredient is suspended in an aqueous continuous phase as a solid state. In the present pesticidal composition, the liquid phase consists essentially of the aqueous continuous phase. Namely, in the present pesticidal composition, the solid water-insoluble pesticidal ingredient substantially exists as fine particles and is surrounded by an aqueous continuous phase dissolving an N-phosphonomethylglycinate. The present pesticidal composition can be clearly distinguished from so-called suspoemulsion, wherein droplets of a water-insoluble solvent are dispersed in the aqueous continuous phase and the water-insoluble pesticidal ingredient is dispersed in the droplets as a solid state.

The present pesticidal composition does not substantially comprise a water-insoluble organic solvent having 10 g/L or less of water solubility at 20° C.

The present pesticidal composition can be produced by making the particles of the solid pesticidal ingredient suspended uniformly in the solution comprising an N-phosphonomethylglycinate, first anionic surfactant, second anionic surfactant, thickener and water.

The solid pesticidal ingredient is usually particles having 20 μm or less of volume median diameter. The solid pesticidal ingredient having 20 μm or less of volume median diameter may be prepared by a method of dry pulverizing; however, it is preferably prepared by wet pulverizing. When the solid pesticidal ingredient is prepared by wet pulverizing to make the volume median diameter 20 μm or less, the present pesticidal composition is preferably produced by the following method.

At first, the solid pesticidal ingredient is added to a mixture of the first anionic surfactant, the second anionic surfactant and water and wet pulverized to give a suspension of the pesticidal ingredient. The method for wet pulverizing is, for example, adding hard sphere beads such as glass beads to a mixture comprising the pesticidal ingredient, the first anionic surfactant, the second anionic surfactant and water, and stirring. Typically, wet pulverizing devises such as wet beads mill (e.g. dyno-mill) and sand grinder are used.

Then, the thickener and the N-phosphonomethylglycinate, and further water if necessary, are added to the suspension of the pesticidal ingredient. Furthermore, auxiliaries for formulation such as antifreezing agent, preservative, stabilizer and coloring agent may be added. The present pesticidal composition can be produced by stirring the mixture well to be uniform.

It is also preferable to add a thickener that is inorganic fine particles to the pesticidal ingredient at wet pulverizing and add a thickener that is a water soluble polysaccharide to the suspension containing the pesticidal ingredient after pulverizing.

Further, a suspension containing the pesticidal ingredient can be prepared by adding the pesticidal ingredient to a mixture containing the second anionic surfactant and water and wet pulverizing. Then, the present pesticidal composition can be produced by adding the first anionic surfactant, thickener and N-phosphonomethylglycinate, and optionally water to the suspension containing the pesticidal ingredient.

The present pesticidal composition is preferably a pesticidal composition wherein (a) 0.5 to 50 w/v % of the water-insoluble solid pesticidal ingredient is suspended as a solid state in the aqueous continuous phase which consists essentially of (b) 5 to 60 w/v % of an N-phosphonomethylglycinate, (c) 0.5 to 15 w/v % of a first anionic surfactant, (d) 0.5 to 10 w/v % of a second anionic surfactant, (e) 0.01 to 10 w/v % of a thickener, (f) 20 to 90 w/v % of water and (g) 0 to 30 w/v % of an auxiliary for formulation such as an antifreezing agent, and more preferably a pesticidal composition wherein (a) 1 to 30 w/v % of the water-insoluble solid pesticidal ingredient is suspended as a solid state in the aqueous continuous phase which consists essentially of (b) 10 to 50 w/v % of an N-phosphonomethylglycinate, (c) 0.5 to 15 w/v % of a first anionic surfactant, (d) 0.5 to 10 w/v % of a second anionic surfactant, (e) 0.01 to 5 w/v % of a thickener, (f) 20 to 90 w/v % of water and (g) 0 to 20 w/v % of an auxiliary for formulation such as an antifreezing agent.

The present pesticidal composition can be used by diluted with water just before the application and applied in a sufficient amount for affording a desirable effect of the pesticidally active ingredient to soil, plants and so on.

The present pesticidal composition can be used as a herbicide for crop field, fallow field, ridge between paddy fields, orchard, pasture, lawn, forest, non-cultivated land and so on, when the solid pesticidal ingredient is flumioxazin. In that case, the dosage depends on a mixing ratio of flumioxazin and an N-phosphonomethylglycinate, kind of the objective weeds, weather condition and so on, and the total amount of the active ingredients is usually 100-5000 g, preferably 200-3000 g per one hectare. When it is applied, the designated amount is diluted with 100-1000 liters of water per one hectare. The dilution is applied by a foliar treatment such as direct application to objective weeds.

An auxiliary agent such as spreading agent may be optionally added to the dilution, and examples of the auxiliary agent include polyoxyethylene resin acid, salts of ligninsulfonic acid, paraffin and petroleum oil. The auxiliary agents on the market such as Agridex (crop oil concentrate produced by Helena) can also be used.

Examples of the weeds controlled by the present pesticidal composition wherein the water-insoluble solid pesticidal ingredient is flumioxazin include broad leaf weeds such as wild buckwheat (*Polygonum convolvulus*), pale smartweed (*Polygonum lapathifolium*), Japanese dock (*Rumex japonicus*), common purslane (*Portulaca oleracea*), common chickweed (*Stellaria media*), common lambs quarters (*Chenopodium album*), redroot pigweed (*Amaranthus retroflexus*), radish (*Raphanus sativus*), wild mustard (*Sinapis arvensis*), shepherds purse (*Capsella bursa-pastoris*), flexuous bittercress (*Cardamine flexuosa*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), cleavers (*Galium aparine*), iveleaf morning glory (*Ipomoea hederacea*), tall morning glory (*Pharbitis purpurea*), field bindweed (*Convolvulus arvensis*), purple dead nettle (*Lamium purpureum*), henbit (*Lamium amplexicaule*), jimsonweed (*Datura stramonium*), black nightshade (*Solanum nigrum*), Persian speedwell (*Veronica persica*), common cocklebur (*Xanthium pensylvanicum*), spiny sowthistle (*Sonchus asper*), common sunflower (*Helianthus annuus*), scentless chamomile (*Matricaria perforata*), corn marigold (*Chrysanthemum segetum*), Japanese mugwort (*Artemisia princeps*) and Sumatra erigeron (*Conysa sumatrensis*); gramineous weeds such as elymus (*Agropyron tsukushiensis* var. *transiens*), barnyardgrass (*Echinochloa crus-galli*), green foxtail (*Setaria viridis*), giant foxtail (*Setaria faberi*), southern crabgrass (*Digitaria ciliaris*), annual bluegrass (*Poa annua*), water foxtail (*Alopecurus geniculatus*), blackgrass (*Alopecurus myosuroides*), oats (*Avena sativa*), wild oats (*Avena fatua*), Johnsongrass (*Sorghum halepense*), quackgrass (*Agropyron repens*) and downey brome (*Bromus tectorum*); Commelinaceae weed such as asiatic dayflower (*Commelina communis*) and bengal dayflower (*Commelina benghalensis*); and Cyperaceae weed such as rice flatsedge (*Cyperus iria*), purple nutsedge (*Cyperus rotundus*) and yellow nutsedge (*Cyperus esculentus*).

EXAMPLES

Hereinafter, the present invention is explained by production examples and so on in more detail; however, the present invention is not restricted to these examples.

Production Example 1

(1) Into a 500 ml-volume stainless steel beaker, 83.0 g of deionized water and 55.2 g of Soprophor FLK (potassium polyoxyethylene tristyrylphenyl ether phosphate (40%) and propylene glycol (60%) produced by Rhodia Nikka) were charged and stirred to be dissolved. Then, 1.1 g of Antifoam C (antifoaming agent, silicone emulsion produced by Dow Corning), 5.5 g of Aerosil COK-84 (thickener, a mixture of silica/aluminum oxide produced by Degussa) and 55.2 g of flumioxazin (content: 99.8%) were added thereto, and further 300 g of glass beads having 1.0 mm of diameter were added. The mixture was stirred at 2000 rpm with Lab-stirrer (produced by Yamato Scientific) at room temperature for 2 hours. Filtering out the glass beads with nylon net afforded a flumioxazin suspension. The volume median diameter of flumioxazin in the suspension measured 2.0 μm with Mastersizer 2000 (produced by Malvern).

(2) Into a 500 ml-volume stainless steel beaker, 297.6 g of deionized water and 2.4 g of Kelzan ASX (acid staple xanthan gum produced by CP Kelco) were charged and stirred with Lab-stirrer (produced by Yamato Scientific) to give an aqueous thickener solution.

(3) Into a 300 ml-volume stainless steel beaker, 72.4 g of the flumioxazin suspension obtained in (1) and 16.0 g of Geronol CF/AR (ammonium polyoxyethylene alkyl ether phosphate (70%) produced by Rhodia Nikka) were charged and stirred at 3000 rpm with Polytoron (homoginizer produced by Kinematica) at room temperature for 5 minutes. Further, 30 g of the aqueous thickener solution obtained in (2) were added thereto and stirred at 3000 rpm at room temperature for 5 minutes. Then, 87.1 g of an aqueous solution of isopropylammonium N-phosphonomethylglycinate (content: 62%) and deionized water were added thereto to make the total 200 ml, and stirred at 3000 rpm at room temperature for 10 minutes to give Pesticidal composition 1.

Production Example 2

The same procedure as Production example 1, except that 32.0 g in place of 16.0 g of ammonium polyoxyethylene alkyl ether phosphate and 25 g in place of 30 g of the aqueous thickener solution obtained in (2) were used, was performed to give Pesticidal composition 2.

Production Example 3

The same procedure as Production example 1, except that 35 g in place of 30 g of the aqueous thickener solution obtained in (2) were used, was performed to give Pesticidal composition 3.

Production Example 4

The same procedure as Production example 1, except that 40 g in place of 30 g of the aqueous thickener solution obtained in (2) were used, was performed to give Pesticidal composition 4.

Production Example 5

(1) Into a 500 ml-volume stainless steel beaker, 82.4 g of deionized water and 54.9 g of Soprophor FLK (potassium polyoxyethylene tristyrylphenyl ether phosphate produced by Rhodia) were charged and stirred to be dissolved. Then, 1.1 g of Antifoam C (antifoaming agent, silicone emulsion produced by Dow Corning), 6.6 g of Aerosil COK-84 (thickener, a mixture of silica/aluminum oxide produced by Degussa) and 54.9 g of flumioxazin (content: 99.2%) were added thereto, and further 300 g of glass beads having 1.0 mm of diameter were added. The mixture was stirred at 2000 rpm with Lab-stirrer (produced by Yamato Scientific) at room temperature for 2 hours. Filtering out the glass beads with nylon net afforded a flumioxazin suspension. The volume median diameter of flumioxazin in the suspension measured 1.9 μm with Mastersizer 2000 (produced by Malvern).

(2) Into a 500 ml-volume stainless steel beaker, 297.6 g of deionized water and 2.4 g of Kelzan ASX (acid staple xanthan gum produced by CP Kelco) were charged and stirred with Lab-stirrer (produced by Yamato Scientific) to give an aqueous thickener solution.

(3) Into a 300 ml-volume stainless steel beaker, 72.8 g of the flumioxazin suspension obtained in (1) and 16.0 g of Geronol CF/AR (ammonium polyoxyethylene alkyl ether phosphate produced by Rhodia Nikka) were charged and stirred at 3000 rpm with Polytoron (homoginizer produced by Kinematica) at room temperature for 5 minutes. Further, 30 g of the aqueous thickener solution obtained in (2) were added thereto and stirred at 3000 rpm at room temperature for 5 minutes. Then, 87.1 g of an aqueous solution of isopropylammonium N-phosphonomethylglycinate (content: 62%) and deionized water were added thereto to make the total 200 ml, and stirred at 3000 rpm at room temperature for 10 minutes to give Pesticidal composition 5.

Production Example 6

The same procedure as Production example 5, except that 35 g in place of 30 g of the aqueous thickener solution obtained in (2) were used, was performed to give Pesticidal composition 6.

Production Example 7

The same procedure as Production example 5, except that 40 g in place of 30 g of the aqueous thickener solution obtained in (2) were used, was performed to give Pesticidal composition 7.

Production Example 8

(1) Into a 500 ml-volume stainless steel beaker, 82.0 g of deionized water and 54.6 g of Soprophor FLK (potassium polyoxyethylene tristyrylphenyl ether phosphate produced by Rhodia) were charged and stirred to be dissolved. Then, 1.1 g of Antifoam C (antifoaming agent, silicone emulsion produced by Dow Corning), 7.7 g of Aerosil COK-84 (thickener, a mixture of silica/aluminum oxide produced by Degussa) and 54.6 g of flumioxazin (content: 99.2%) were added thereto, and further 300 g of glass beads having 1.0 mm of diameter were added. The mixture was stirred with Three-One Motor (stirrer produced by Shinto Kagaku) for 1.5 hours. Filtering out the glass beads afforded a flumioxazin suspension. The volume median diameter of flumioxazin in the suspension measured 2.0 μm with Mastersizer 2000 (produced by Malvern).

(2) Into a 500 ml-volume stainless steel beaker, 297.6 g of deionized water and 2.4 g of Kelzan ASX (acid staple xanthan gum produced by CP Kelco) were charged and stirred with Lab-stirrer to give an aqueous thickener solution.

(3) Into a 300 ml-volume stainless steel beaker, 73.2 g of the flumioxazin suspension obtained in (1) and 16.0 g of Geronol CF/AR (ammonium polyoxyethylene alkyl ether phosphate produced by Rhodia Nikka) were charged and stirred at 3000 rpm with Polytoron (homoginizer produced by Kinematica) at room temperature for 5 minutes. Further, 30 g of the aqueous thickener solution obtained in (2) were added thereto and stirred at 3000 rpm at room temperature for 5 minutes. Then, 87.1 g of an aqueous solution of isopropylammonium N-phosphonomethylglycinate (content: 62%) and deionized water were added thereto to make the total 200 ml, and stirred at 3000 rpm at room temperature for 10 minutes to give Pesticidal composition 8.

Production Example 9

The same procedure as Production example 8, except that 35 g in place of 30 g of the aqueous thickener solution obtained in (2) were used, was performed to give Pesticidal composition 9.

Production Example 10

(1) Into a 500 ml-volume stainless steel beaker, 68.0 g of deionized water, 45.2 g of Soprophor FLK (potassium polyoxyethylene tristyrylphenyl ether phosphate produced by Rhodia) and 36.2 g of Geronol CF/AR (ammonium polyoxyethylene alkyl ether phosphate produced by Rhodia) were charged and stirred to be dissolved. Then, 0.9 g of Antifoam C (antifoaming agent, silicone emulsion produced by Dow Corning), 4.5 g of Aerosil COK-84 (thickener, a mixture of silica/aluminum oxide produced by Degussa) and 45.2 g of flumioxazin (content: 99.2%) were added thereto, and further 300 g of glass beads having 1.0 mm of diameter were added. The mixture was stirred with Three-One Motor (stirrer produced by Shinto Kagaku) for 2 hours. Filtering out the glass beads afforded a flumioxazin suspension. The volume median diameter of flumioxazin in the suspension measured 2.0 μm with Mastersizer 2000 (produced by Malvern).

(2) Into a 500 ml-volume stainless steel beaker, 297.6 g of deionized water and 2.4 g of Kelzan ASX (acid staple xanthan gum produced by CP Kelco) were charged and stirred with Lab-stirrer (produced by Yamato Scientific) to give an aqueous thickener solution.

(3) Into a 300 ml-volume stainless steel beaker, 88.4 g of the flumioxazin suspension obtained in (1) and 30 g of the aqueous thickener solution obtained in (2) were added thereto and stirred at 3000 rpm with Polytoron (homoginizer produced by Kinematica) for 5 minutes. Then, 87.1 g of an aqueous solution of isopropylammonium N-phosphonomethylglycinate (content: 62%) and deionized water were added thereto to make the total 200 ml, and stirred at 3000 rpm for 10 minutes to give Pesticidal composition 10.

Production Example 11

The same procedure as Production example 10, except that 40 g in place of 30 g of the aqueous thickener solution obtained in (2) were used, was performed to give Pesticidal composition 11.

Production Example 12

(1) To a mixture of 35.2 parts of deionized water, 25.4 parts of Soprophor FLK (potassium polyoxyethylene tristyrylphenyl ether phosphate produced by Rhodia), 0.3 parts of Antifoam C emulsion (antifoaming agent, silicone emulsion produced by Dow Corning) and 25.4 parts of flumioxazin (content: 99.2%), 130 parts of glass beads having 1.0 mm of diameter were added and stirred with Three-One Motor (stirrer produced by Shinto Kagaku) for 2 hours. Filtering out the glass beads afforded a flumioxazin suspension. The volume median diameter in the suspension measured 2.0 µm with Mastersizer 2000 (produced by Malvern).
(2) To the flumioxazin suspension obtained in (1), 0.2 parts of Antifoam C emulsion (antifoaming agent, silicone emulsion produced by Dow Corning), 87.5 parts of Geronol CF/AR (ammonium polyoxyethylene alkyl ether phosphate produced by Rhodia), 25.4 parts of Aerosil COK-84 (thickener, a mixture of silica/aluminum oxide produced by Degussa), 655.9 parts of an aqueous solution of isopropylammonium N-phosphonomethylglycinate (content: 62%) and 95.4 parts of deionized water were added and stirred at 5000 rpm with Polytoron (homoginizer produced by Kinematica,) at room temperature for 10 minutes to give Pesticidal composition 12.

Production Example 13

(1) To a mixture of 35.2 parts of deionized water, 25.4 parts of Soprophor FLK (potassium polyoxyethylene tristyrylphenyl ether phosphate produced by Rhodia), 0.3 parts of Antifoam C (antifoaming agent, silicone emulsion produced by Dow Corning) and 25.4 parts of flumioxazin (content: 99.2%), 130 parts of glass beads having 1.0 mm of diameter were added and stirred with Three-One Motor (stirrer produced by Shinto Kagaku) for 2 hours. Filtering out the glass beads afforded a flumioxazin suspension. The volume median diameter of flumioxazin in the suspension measured 2.0 µm with Mastersizer 2000 (produced by Malvern).
(2) To the flumioxazin suspension obtained in (1), 0.2 parts of Antifoam C emulsion (antifoaming agent, silicone emulsion produced by Dow Corning), 52.5 parts of Geronol CF/AR (ammonium polyoxyethylene alkyl ether phosphate produced by Rhodia), 25.4 parts of Aerosil COK-84 (thickener, a mixture of silica/aluminum oxide produced by Degussa), 655.9 parts of an aqueous solution of isopropylammonium N-phosphonomethylglycinate (content: 62%), 27.1 parts of polypropylene glycol and 152.7 parts of deionized water were added and stirred at 5000 rpm with Polytoron (homoginizer produced by Kinematica) at room temperature for 10 minutes to give Pesticidal composition 13.

Production Example 14

The same procedure as Production example 1, except that 2.4 g of Kelzan S (xanthan gum produced by CP Kelco) in place of 2.4 g of Kelzan ASX (acid staple xanthan gum produced by CP Kelco) and 40 g in place of 30 g of the aqueous thickener solution obtained in (2) were used, was performed to give Pesticidal composition 14.

Production Example 15

(1) Into a 500 ml-volume stainless steel beaker, 83.0 g of deionized water and 55.2 g of Soprophor FLK (potassium polyoxyethylene tristyrylphenyl ether phosphate (40%) and propylene glycol (60%) produced by Rhodia Nikka) were charged and stirred to be dissolved. Then, 1.1 g of Antifoam C (antifoaming agent, silicone emulsion produced by Dow Corning), 5.5 g of Aerosil COK-84 (thickener, a mixture of silica/aluminum oxide produced by Degussa) and 55.2 g of flumiclorac-pentyl (content: 97.7%) were added thereto, and further 300 g of glass beads having 1.0 mm of diameter were added. The mixture was stirred at 2000 rpm with Lab-stirrer (produced by Yamato Scientific) at room temperature for 2 hours. Filtering out the glass beads with nylon net afforded a flumiclorac-pentyl suspension. The volume median diameter of flumiclorac-pentyl in the suspension measured 1.8 µm with Mastersizer 2000 (produced by Malvern).
(2) Into a 500 ml-volume stainless steel beaker, 297.6 g of deionized water and 2.4 g of Kelzan ASX (acid staple xanthan gum produced by CP Kelco) were charged and stirred with Lab-stirrer (produced by Yamato Scientific) to give an aqueous thickener solution.
(3) Into a 300 ml-volume stainless steel beaker, 72.4 g of the flumiclorac-pentyl suspension obtained in (1) and 16.0 g of Geronol CF/AR (ammonium polyoxyethylene alkyl ether phosphate (70%) produced by Rhodia Nikka) were charged and stirred at 3000 rpm with Polytoron (homoginizer produced by Kinematica) at room temperature for 5 minutes. Further, 30 g of the aqueous thickener solution obtained in (2) were added thereto and stirred at 3000 rpm at room temperature for 5 minutes. Then, 87.1 g of an aqueous solution of isopropylammonium N-phosphonomethylglycinate (content: 62%) and deionized water were added thereto to make the total 200 ml, and stirred at 3000 rpm at room temperature for 10 minutes to give Pesticidal composition 15.

Production Example 16

The same procedure as Production example 15 (1), except that 55.2 g of diclocymet (content: 98.7%) in place of 55.2 g of flumiclorac-pentyl (content: 97.7%) were used, was performed to give a diclocymet suspension. (volume median diameter: 1.9 µm)
Further, after the procedure as Production example 15 (2), the same procedure as Production example 15 (3), except that 72.4 g of the diclocymet suspension described above in place of 72.4 g of the flumiclorac-pentyl suspension were used, was performed to give Pesticidal composition 16.

Production Example 17

The same procedure as Production example 15 (1), except that 55.2 g of bensultap (content: 96.0%) in place of 55.2 g of flumiclorac-pentyl (content: 97.7%) were used, was performed to give a bensultap suspension. (volume median diameter: 2.9 µm)
Further, after the procedure as Production example 15 (2), the same procedure as Production example 15 (3), except that 72.4 g of the bensultap suspension described above in place of 72.4 g of the flumiclorac-pentyl suspension were used, was performed to give Pesticidal composition 17.

Production Example 18

The same procedure as Production example 15 (1), except that 55.2 g of diflufenican (content: 98.5%) in place of 55.2 g of flumiclorac-pentyl (content: 97.7%) were used, was performed to give a diflufenican suspension. (volume median diameter: 2.6 μm)

Further, after the procedure as Production example 15 (2), the same procedure as Production example 15 (3), except that 72.4 g of the diflufenican suspension described above in place of 72.4 g of the flumiclorac-pentyl suspension were used, was performed to give Pesticidal composition 18.

Production Example 19

Flumioxazin (content: 99.8%) was dry pulverized with air mill for 60 minutes to give flumioxazin powders having 2.8 μm of volume median diameter.

To a mixture of 15 g of deionized water and 10 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 1.0 g of the flumioxazin powders obtained above and 8.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

To 19.84 g of deionized water, 0.16 g of Kelzan ASX (acid staple xanthan gum produced by CP Kelco) were added and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension, 43.55 g of an aqueous solution of isopropylammonium N-phosphonomethylglycinate (content: 62%) and 1.25 g of deionized water were added and stirred at 5000 rpm with Polytoron (homoginizer produced by Kinematica) at room temperature for 5 minutes to give Pesticidal composition 19.

Production Example 20

To a mixture of 15 g of deionized water and 10 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 1.0 g of the flumioxazin powders obtained in Production example 19 and 8.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 19.84 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension, 16.12 g of an aqueous solution of isopropylammonium N-phosphonomethylglycinate (content: 62%) and 28.68 g of deionized water were added and stirred at 5000 rpm with Polytoron (homoginizer produced by Kinematica) at room temperature for 5 minutes to give Pesticidal composition 20.

Production Example 21

To a mixture of 15 g of deionized water and 10 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 10 g of the flumioxazin powders obtained in Production example 19 and 8.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 19.84 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension, 16.12 g of an aqueous solution of isopropylammonium N-phosphonomethylglycinate (content: 62%) and 19.68 g of deionized water were added and stirred at 5000 rpm with Polytoron (homoginizer produced by Kinematica) at room temperature for 5 minutes to give Pesticidal composition 21.

Production Example 22

To 10 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 30.0 g of the flumioxazin powders obtained in Production example 19 and 8.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 18.39 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension and 32.25 g of an aqueous solution of isopropylammonium N-phosphonomethylglycinate (content: 62%) were added and stirred at 5000 rpm with Polytoron (homoginizer produced by Kinematica) at room temperature for 5 minutes to give Pesticidal composition 22.

Production Example 23

To a mixture of 14.68 g of deionized water and 10 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 30.0 g of the flumioxazin powders obtained in Production example 19 and 8.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 19.84 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension and 16.12 g of an aqueous solution of isopropylammonium N-phosphonomethylglycinate (content: 62%) were added and stirred at 5000 rpm with Polytoron (homoginizer produced by Kinematica) at room temperature for 5 minutes to give Pesticidal composition 23.

Production Example 24

To a mixture of 7.26 g of deionized water and 1.0 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 10.0 g of the flumioxazin powders obtained in Production example 19 and 17.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 19.84 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension and 43.54 g of an aqueous solution of isopropylammonium N-phosphonomethylglycinate (content: 62%) were added and stirred at 5000 rpm with Polytoron (homoginizer produced by Kinematica) at room temperature for 5 minutes to give Pesticidal composition 24.

Production Example 25

To a mixture of 7.26 g of deionized water and 9.0 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 10.0 g of the flumioxazin powders obtained in Production example 19 and 9.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 19.84 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension and 43.54 g of an aqueous solution of isopropylammonium N-phosphonomethylglycinate (content: 62%) were added and stirred at 5000 rpm with Polytoron (homoginizer produced by Kinematica) at room temperature for 5 minutes to give Pesticidal composition 25.

Production Example 26

To a mixture of 7.26 g of deionized water and 17.0 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 10.0 g of the flumioxazin powders obtained in Production example 19 and 1.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 19.84 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension and 43.54 g of an aqueous solution of isopropylammonium N-phosphonomethylglycinate (content: 62%) were added and stirred at 5000 rpm with Polytoron (homoginizer produced by Kinematica) at room temperature for 5 minutes to give Pesticidal composition 26.

Production Example 27

To 25.0 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 10.0 g of the flumioxazin powders obtained in Production example 19 and 16.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) and 4.1 g of deionized water were added to 43.54 g of an aqueous solution of isopropylammonium N-phosphonomethylglycinate (content: 62%), stirred with Three-One Motor (stirrer produced by Shinto Kagaku) at 60° C. for 2 hours and cooled to 25° C. The above-mentioned flumioxazin suspension was added thereto and stirred at 5000 rpm with Polytoron (homoginizer produced by Kinematica) at room temperature for 5 minutes to give Pesticidal composition 27.

Production Example 28

To 1 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 1.0 g of the flumioxazin powders obtained in Production example 19 and 17.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) and 4.1 g of deionized water were added to 79.64 g of an aqueous solution of isopropylammonium N-phosphonomethylglycinate (content: 62%), stirred with Three-One Motor (stirrer produced by Shinto Kagaku) at 60° C. for 2 hours and cooled to 25° C. The above-mentioned flumioxazin suspension was added thereto and stirred at 5000 rpm with Polytoron (homoginizer produced by Kinematica) at room temperature for 5 minutes to give Pesticidal composition 28.

Production Example 29

To 15.0 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 1.0 g of the flumioxazin powders obtained in Production example 19 and 3.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension. To 79.64 g of an aqueous solution of isopropylammonium N-phosphonomethylglycinate (content: 62%), 0.16 g of Kelzan ASX (acid staple xanthan gum produced by CP Kelco) were added and stirred with Three-One Motor (stirrer produced by Shinto Kagaku) at 60° C. for 2 hours and cooled to 25° C. The above-mentioned flumioxazin suspension was added thereto and stirred at 5000 rpm with Polytoron (homoginizer produced by Kinematica) at room temperature for 5 minutes to give Pesticidal composition 29.

Production Example 30

Flumioxazin (content: 99.8%) was dry pulverized with air mill for 60 minutes to give flumioxazin powders having 2.8 µm of volume median diameter.

To a mixture of 10.26 g of deionized water and 1.0 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 10.0 g of the flumioxazin powders obtained above and 10.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

To 19.34 g of deionized water, 0.16 g of Kelzan ASX (acid staple xanthan gum produced by CP Kelco) were added and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension, 43.54 g of an aqueous solution of isopropylammonium N-phosphonomethylglycinate (content: 62%) and 4.5 g of propylene glycol were added and stirred at 5000 rpm with Polytoron (homoginizer produced by Kinematica) at room temperature for 5 minutes to give Pesticidal composition 30.

Production Example 31

To a mixture of 10.26 g of deionized water and 5.0 g of Soprophor FLK (potassium polyoxyethylene tristyrylphenyl ether phosphate (40%) and propylene glycol (60%) produced by Rhodia Nikka), 0.2 g of Antifoam C (antifoaming agent, silicone emulsion produced by Dow Corning), 1.0 g of Aerosil COK-84 (thickener, a mixture of silica/aluminum oxide produced by Degussa), 10.0 g of the flumioxazin powders obtained in Production example 30 and 10.0 g of Geronol CF/AR (ammonium polyoxyethylene alkyl ether phosphate (70%) produced by Rhodia Nikka) were added and stirred at 5000 rpm with Polytoron (homoginizer produced by Kinematica) at room temperature for 5 minutes to give a flumioxazin suspension.

Then, 0.16 g of Kelzan ASX (acid staple xanthan gum produced by CP Kelco) were added to 17.34 g of deionized water and stirred with Three-One Motor (stirrer produced by Shinto Kagaku) at 60° C. for 2 hours to give an aqueous thickener solution. After the aqueous thickener solution was cooled to 25° C., the above-mentioned flumioxazin suspension, 43.54 g of an aqueous solution of isopropylammonium N-phosphonomethylglycinate (content: 62%) and 2.5 g of propylene glycol were added and stirred at 5000 rpm with Polytoron (homoginizer produced by Kinematica) at room temperature for 5 minutes to give Pesticidal composition 31.

Reference Production Example 1

(1) To a mixture of 35.2 parts of deionized water, 2.5 parts of Reax 910 (sodium ligninsulfonate produced by Westvaco), 0.3 parts of Antifoam C emulsion (antifoaming agent, silicone emulsion produced by Dow Corning) and 25.4 parts of flumioxazin (content: 99.2%), 130 parts of glass beads having 1.0 mm of diameter were added and stirred with Three-One Motor (stirrer produced by Shinto Kagaku) for 2 hours. After filtering out the glass beads, a flumioxazin suspension was obtained. Measurement of the flumioxazin suspension with Mastersizer 2000 (produced by Malvern) gave 1.8 µm of volume median diameter of flumioxazin.

(2) To the flumioxazin suspension obtained in (1), 0.2 parts of Antifoam C (antifoaming agent, silicone emulsion produced by Dow Corning), 50.8 parts of Arcard 16-50 (hexadecyltrimethylammonium chloride produced by Lion Akzo), 33.9 parts of Emalsogen M (fatty alcohol polyglycol ether produced by Clariant), 25.4 parts of Aerosil COK-84 (thickener, a mixture of silica/aluminum oxide produced by Degussa), 655.9 parts of an aqueous solution of isopropylammonium N-phosphonomethylglycinate (content: 62%), 42.4 parts of polypropylene glycol and 128.0 parts of deionized water were added and stirred at 5000 rpm with Polytoron (homoginizer produced by Kinematica) at room temperature for 10 minutes to give Reference pesticidal composition.

Test Example 1

Each of the Pesticidal compositions 1, 3, 4, 5, 6, 7, 8, 9, 15, 16, 17 and 18 was charged into a 100 ml-volume glass tube (diameter: 35 mm, depth: 110 mm) and about 80% of the tubes were filled. It was allowed to stand at room temperature for two months. After that, all of the Pesticidal compositions were observed to be kept stable suspension state and not separated.

Test Example 2

The Pesticidal composition 2 was charged into a 100 ml-volume glass tube (diameter: 35 mm, depth: 110 mm) and about 80% of the tube were filled. It was allowed to stand at 54° C. for one month. Then, it was observed to be separated a little at the top, but the height of the separated transparent layer is 4% of the whole composition.

Test Example 3

Each of the Pesticidal compositions 12 and 13 and the reference pesticidal composition was charged into a 100 ml-volume glass tube (diameter: 35 mm, depth: 110 mm) and about 80% of the tubes were filled. It was allowed to stand for three days and observed. The results are given in Table 1.

TABLE 1

| Compositions | Status after 3 days | Rate of Separation*1 |
| --- | --- | --- |
| Pesticidal composition 12 | Homogeneous (No separation) | 0% |
| Pesticidal composition 13 | Homogeneous (No separation) | 0% |
| Reference pesticidal composition | Transparent separated layer at bottom | 8% |

*1: Rate of Separation (%) = [Height of the transparent part/layer (mm)/Height of the total (mm)] × 100

Test Example 4

An aqueous dilution was prepared by diluting a designated amount of the Pesticidal composition 2 with water. The aqueous dilution was applied to common cocklebur (*Xanthium pensylvanicum*), velvetleaf (*Abutilon theophrasti*), giant foxtail (*Setaria faberi*) and barnyardgrass (*Echinochloa crusgalli*) grown in the crop field by a foliar treatment at a rate of 236 L/ha (2 L/ha in the amount of the aqueous pesticidal flowable composition 2). The results of the observation 18 days after treatment are given in Table 2. The herbicidal activity is evaluated at 11 levels with indices of "0", "1", "2", "3", "4", "5", "6", "7", "8", "9" and "10", wherein 0 means that there was no or little difference in the degree of growth between the treated weeds and the untreated weeds at the time of evaluation, and 10 means that the weeds died completely or their growth was completely inhabited.

TABLE 2

| | Herbicidal effect | | | |
| --- | --- | --- | --- | --- |
| Composition | common cocklebur | velvetleaf | giant foxtail | Barnyard-grass |
| Pesticidal composition 2 | 10 | 10 | 10 | 9 |

The present pesticidal composition is excellent in suspension stability; therefore, it is useful for pesticidal formulation comprising a water-insoluble pesticidal ingredient and a salt of N-phosphonomethylglycine which is a pesticidal ingredient being freely soluble in water.

The invention claimed is:

1. A pesticidal composition which consists essentially of (a) 1 to 30 w/v % of N-(7-fluoro-3,4-dihydro-3-oxo-4-prop-2-ynyl-2H-1,4-benzoxazin-6-yl)cyclohex-1-ene-1,2-dicarboxamide, (b) 10 to 50 w/v % of a salt of N-phosphonomethylglycine, (c) 0.5 to 15 w/v % of a salt of polyoxyalkylene alkyl ether phosphate ester, (d) 0.5 to 10 w/v % of a salt of polyoxyalkylene polystyrylphenyl ether phosphate ester, (e) 0.01 to 5 w/v % of a thickener which comprises (e-1) inorganic solid fine powder and (e-2) a water-soluble polysaccharide, (f) 20 to 90 w/v % of water and (g) 0 to 20 w/v % of an auxiliary for formulation, wherein said pesticidal ingredient is suspended in the aqueous continuous phase as solid state.

2. The pesticidal composition according to claim 1, wherein (g) the auxiliary for formulation is at least one selected from the group consisting of antifreezing agent, antifoaming agent, preservative, stabilizer, coloring agent, perfume, synergist and safener.

3. A method for controlling weeds which comprises applying a dilution of the pesticidal composition described in claim 1 or 2 to weeds by foliar treatment.

4. A method for producing a pesticidal composition which comprises wet pulverizing a mixture consisting essentially of (a) 1 to 30 w/v % of N-(7-fluoro-3,4-dihydro-3-oxo-4-prop-2-ynyl-2H-1,4-benzoxazin-6-yl)cyclohex-1-ene-1,2-dicarboxamide, (c) 0.5 to 15 w/v % of a salt of polyoxyalkylene alkyl ether phosphate ester, (d) 0.5 to 10 w/v % of a salt of polyoxyalkylene polystyrylphenyl ether phosphate ester and (f) 20 to 90 w/v % of water to give a suspension, and mixing the obtained suspension with (b) 10 to 50 w/v % of a salt of N-phosphonomethylglycine and (e) 0.01 to 5 w/v % of a thickener which comprises (e-1) inorganic solid fine powder and (e-2) a water-soluble polysaccharide.

5. A method for producing a pesticidal composition which comprises wet pulverizing a mixture consisting essentially of (a) 1 to 30 w/v % of N-(7-fluoro-3,4-dihydro-3-oxo-4-prop-2-ynyl-2H-1,4-benzoxazin-6-yl)cyclohex-1-ene-1,2-dicarboxamide, (c) 0.5 to 15 w/v % of a salt of polyoxyalkylene alkyl ether phosphate ester, (d) 0.5 to 10 w/v % of a salt of polyoxyalkylene polystyrylphenyl ether phosphate ester, (e-1) inorganic solid fine powder and (f) 20 to 90 w/v % of water to give a suspension, and mixing the obtained suspension with (b) 10 to 50 w/v % of a salt of N-phosphonomethylglycine and (e-2) a water soluble polysaccharide;
wherein a total content of the (e-1) inorganic solid fine powder and the (e-2) water soluble polysaccharide is 0.01 to 5 w/v %.

6. A method for producing a pesticidal composition which comprises wet pulverizing a mixture consisting essentially of (a) 1 to 30 w/v % of N-(7-fluoro-3,4-dihydro-3-oxo-4-prop-2-ynyl-2H-1,4-benzoxazin-6-yl)cyclohex-1-ene-1,2-dicarboxamide, (d) 0.5 to 10 w/v % of a salt of polyoxyalkylene polystyrylphenyl ether phosphate ester, (e-1) inorganic solid fine powder and (f) 20 to 90 w/v % of water to give a suspension, and mixing the obtained suspension with (b) 10 to 50 w/v % of a salt of N-phosphonomethylglycine, (c) 0.5 to 15 w/v % of a salt of polyoxyalkylene alkyl ether phosphate ester and (e-2) a water soluble polysaccharide;
wherein a total content of the (e-1) inorganic solid fine powder and the (e-2) water soluble polysaccharide is 0.01 to 5 w/v %.

* * * * *